United States Patent [19]

Downing et al.

[11] Patent Number: 5,414,010
[45] Date of Patent: May 9, 1995

[54] DIMERIC BENZIMIDAZOLES AS CENTRAL NERVOUS SYSTEM AGENTS

[75] Inventors: Dennis M. Downing; Lawrence D. Wise; Jonathan L. Wright, all of Ann Arbor, Mich.

[73] Assignee: Warner-Lambert Company, Morris Plains, N.J.

[21] Appl. No.: 240,354

[22] Filed: May 10, 1994

[51] Int. Cl.⁶ .................. A61K 31/415; C07D 401/14; C07D 403/06; C07D 403/14
[52] U.S. Cl. ..................................... 514/316; 514/253; 514/322; 514/394; 544/357; 544/370; 546/187; 546/189; 548/305.7; 548/400; 548/306.1; 548/571; 564/441
[58] Field of Search ....................... 548/305.7; 546/199, 546/187; 544/370, 357; 514/253, 322, 394, 316

[56] References Cited

U.S. PATENT DOCUMENTS 4,537,974  8/1985  Lau .................................... 548/305.7
5,159,083  10/1992  Thurkauf et al. ................ 548/335.5

*Primary Examiner*—Emily Bernhardt
*Attorney, Agent, or Firm*—Francis J. Tinney

[57] ABSTRACT

Dimeric benzimidazoles are described, as well as methods for the preparation and pharmaceutical composition of same, which are useful as central nervous system agents and are particularly useful as antipsychotic agents and for the treatment of disorders which respond to dopaminergic blockade including psychotic depression, substance abuse, and compulsive disorders.

5 Claims, No Drawings

DIMERIC BENZIMIDAZOLES AS CENTRAL NERVOUS SYSTEM AGENTS

BACKGROUND OF THE INVENTION

The present invention relates to novel substituted dimeric benzimidazoles useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are dopaminergic agents useful as antipsychotic agents for treating psychoses such as schizophrenia.

Dopamine D2 antagonists are established as antipsychotic agents. More recently, the dopamine D3 receptor has been identified (Schwartz Jean-Charles, et al., The Dopamine D3 Receptor as a Target for Antipsychotics. In *Novel Antipsychotic Drugs*, Meltzer H. Y., Ed., Raven Press, New York, 1992, p. 135–144). On the basis of the localization of the dopamine D3 receptor in the limbic area of the brain, a selective D3 antagonist should show antipsychotic activity but not have the neurological side effects of D2 antagonists (Sokoloff P., et al., Molecular Cloning and Characterization of a Novel Dopamine Receptor (D3) as a Target for Neuroleptics, *Nature*, 347:146 (1990); Sokoloff P., et al., Localization and Function of the D3 Dopamine Receptor, *Arzneim.-Forsch./Drug Res.*, 42(1):224, (1992)).

The compounds of the present invention are also useful for the treatment of disorders which respond to dopaminergic blockade which include psychotic depression, substance abuse (Caine S. B. and Koob G. F., Modulation of Cocaine Self-Administration in the Rat Through D-3 Dopamine Receptors, *Science*, 260:1814 (1993)), and compulsive disorders (Goodman W. K., et al., The role of serotonin and dopamine in the pathophysiology of obsessive compulsive disorder, *International Clinical Psychopharmacology*, 7(Supp. 1):35 (1992)).

We have surprisingly and unexpectedly found that a series of dimeric benzimidazoles are dopaminergic agents which bind selectively to the dopamine D3 receptor and are thus useful as antipsychotic agents for treating psychoses such as schizophrenia.

SUMMARY OF THE INVENTION

Accordingly, the present invention is a compound of Formula I

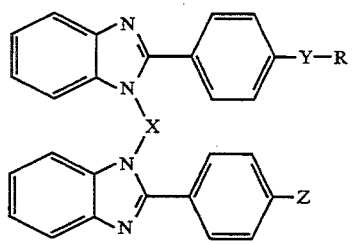

wherein R is

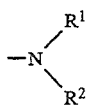

wherein
$R^1$ and $R^2$ are each the same or different and each is
  alkyl of from 1 to 6 carbon atoms,
  alkenyl of from 2 to 6 carbon atoms,
  alkynyl of from 2 to 6 carbon atoms,
  arylalkyl wherein alkyl is from 1 to 6 carbon atoms,
  2-thienylalkyl wherein alkyl is from 1 to 6 carbon atoms or $R^1$ and $R^2$ together with the nitrogen which they substitute form a 5-membered or 6-membered ring or

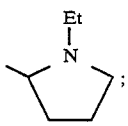

X is
  alkyl of from 2 to 6 carbon atoms,
  alkenyl of from 2 to 6 carbon atoms, or
  alkynyl of from 2 to 6 carbon atoms;
Y is $-O(CH_2)_n-$ wherein n is an integer of from 2 to 6, or

wherein p is zero or an integer of from 1 to 6; and
Z is
  hydrogen,
  hydroxyl,
  alkyl of from 1 to 6 carbon atoms,
  alkoxy of from 1 to 6 carbon atoms, or
  Y—R wherein Y and R are as defined above; and
    corresponding isomers thereof; or a pharmaceutically acceptable acid addition salt thereof.

As dopaminergic agents selective for the dopamine D3 receptor subtype, the compounds of Formula I are useful as antipsychotic agents for treating psychoses such as schizophrenia. They are also useful for the treatment of disorders which respond to dopaminergic blockade. Thus, other embodiments of the present invention include the treatment, by a compound of Formula I, of psychotic depression, substance abuse, and compulsive disorders.

A still further embodiment of the present invention is a pharmaceutical composition for administering an effective amount of a compound of Formula I in unit dosage form in the treatment methods mentioned above. Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "alkenyl" means a straight or branched unsaturated hydrocarbon radical having from 2 to 6 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, and the like.

The term "alkynyl" means a straight or branched triple bonded unsaturated hydrocarbon radical having from 2 to 6 carbon atoms and includes, for example, ethynyl, 2-propynyl, 1-butynyl, 2-butynyl, 3-butynyl, 1-pentynyl, 3-pentynyl, 1-hexynyl, 2-hexynyl, 3-hexynyl, and the like.

"Alkoxy" and "thioalkoxy" are O-alkyl or S-alkyl of from 1 to 6 carbon atoms as defined above for "alkyl".

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, or 1,3-benzodioxol-5-yl.

The term "arylalkyl" means an aromatic radical attached to an alkyl radical wherein aryl and alkyl are as defined above, for example, benzyl, fluorenylmethyl, and the like.

The term "2-thienylalkyl" means a 2-thienyl radical attached to an alkyl radical wherein alkyl is as defined above.

"Halogen" is fluorine, chlorine, bromine, or iodine.

"Alkali metal" is a metal in Group IA of the periodic table and includes, for example, lithium, sodium, potassium, and the like.

The compounds of Formula I are capable of further forming pharmaceutically acceptable acid addition salts. These forms are within the scope of the present invention.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts" *Journal of Pharmaceutical Science*, 66:1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess asymmetric carbon atoms (optical centers); the racemates as well as the individual enantiomers are intended to be encompassed within the scope of the present invention. Additionally, certain of the compounds of the present invention may exist as a mixture of cis and trans isomers or as the individual cis and trans isomers. The mixture of isomers as well as the individual isomers are intended to be encompassed within the scope of the present invention.

A preferred compound of Formula I is one wherein R is

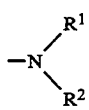

wherein $R^1$ and $R^2$ are each the same or different and each is
methyl,
ethyl,
n-propyl,
isopropyl,
n-butyl,
sec-butyl,
isobutyl,
tert-butyl,
propargyl,
2-phenylethyl,
2-thienyl-2-ethyl or $R^1$ and $R^2$ together with the nitrogen which they substitute form a 1-piperidinyl or 1-pyrrolidinyl ring or

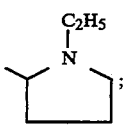

X is n-butyl or 2-butenyl;
Y is
—O(CH$_2$)$_2$—,
—O(CH$_2$)$_3$—,
—O(CH$_2$)$_4$—,

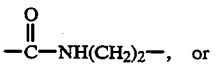, or

;

Z is
hydrogen,
hydroxyl,
methoxy, or

Y—R wherein Y and R are as defined above; and corresponding isomers thereof; or a pharmaceutically acceptable acid addition salt thereof.
Particularly valuable are:

E-1,1'-(2-butene-1,4-diyl)bis[2-[4-[3-(1-pyrrolidinyl)propoxy]phenyl]-1H-benzimidazole;
E-(3-{4-[1-(4-{2-[4-(3-dipropylaminopropoxy)phenyl]benzoimidazol-1-yl}but-2-enyl)-1H-benzoimidazol-2-yl]phenoxy}proppropyl)dipropylamine;
Z-(3-{4-[1-(4-{2-[4-(3-diethylaminopropoxy)phenyl]benzoimidazol-1-yl}but-2-enyl)-1H-benzoimidazol-2-yl]phenoxy}propyl)diethylamine;
(3-{4-[1-(4-{2-[4-(3-diethylaminopropoxy)phenyl]benzoimidazol-1-ylmethyl}benzyl)-1H-benzoimidazol-2-yl]phenoxy}propyl)diethylamine;
E-(3-{4-[1-(4-{2-[4-(3-dimethylaminopropoxy)phenyl]benzoimidazol-1-yl}but-2-enyl)-1H-benzoimidazol-2-yl]phenoxy}propyl)diethylamine;
E-1,1'-(2-butene-1,4-diyl)bis[2-[4-[3-(1-piperidinyl)propoxy]phenyl]-1H-benzimidazole;
E-(3-{3-[1-(4-{2-[3-(3-diethylaminopropoxy)phenyl]benzoimidazol-1-yl}but-2-enyl)-1H-benzoimidazol-2-yl]phenoxy}propyl)diethylamine;
E-dibutyl-(3-{4-[1-(4-{2-[4-(3-dibutylaminopropoxy)phenyl]benzoimidazol-1-yl}but-2-enyl)-1H-benzoimidazol-2-yl]phenoxy}propyl)amine;
E-isopropyl-[3-(4-{1-[4-(2-{4-[3-(isopropylmethylamino)propoxy]phenyl}benzoimidazol-1-yl)but-2-enyl]-1H-benzoimidazol-2-yl}phenoxy)propyl]methylamine;
E-(3-{4-[1-(4-{2-[4-(3-diethylaminopropoxy)phenyl]benzoimidazol-1-yl}but-2-enyl)-1H-benzoimidazol-2-yl]phenoxy}propyl)diethylamine;
(3-{4-[1-(4-{2-[4-(3-dipropylaminopropoxy)phenyl]benzoimidazol-1-yl}butyl)-1H-benzoimidazol-2-yl]phenoxy}propyl)dipropylamine;
(3-{4-[1-(4-{2-[4-(3-diethylaminopropoxy)phenyl]benzoimidazol-1-yl}butyl)-1H-benzoimidazol-2-yl]phenoxy}propyl)diethylamine;
diethyl-[3-(4-{1-[4-(2-phenylbenzoimidazol-1-yl)but-2-enyl]-1H-benzoimidazol-2-yl}phenoxy)propyl]amine;
diethyl-{3-[4-(1-{4-[2-(4-methoxyphenyl)benzoimidazol-1-yl]but-2-enyl}-1H-benzoimidazol-2-yl)phenoxy]propyl}amine;
E-[3-(4-{1-[4-(2-{4-[3-(4-phenylpiperazin-1-yl)propoxy]phenyl}benzoimidazol-1-yl)but-2-enyl]-1H-benzoimidazol-2-yl}phenoxy)propylamine;
4,4'-(1,4-butanediyldi-1H-benzimidazol-1,2-diyl)bis[N-[(1-ethyl-2-pyrrolidinyl)methyl]benzamide; and
4,4'-(1,4-butanediyldi-1H-benzimidazol-1,2-diyl)bis[N-[2-(diethylamino)ethyl]benzamide;

or a pharmaceutically acceptable acid addition salt thereof.

The compounds of Formula I are valuable dopaminergic agents. Dopamine D2 antagonists are established as antipsychotic agents. More recently, the dopamine D3 receptor has been identified. On the basis of the localization of the dopamine D3 receptor in the limbic area of the brain, a selective D3 antagonist should show antipsychotic activity but not have the neurological side effects of D2 antagonists. The tests employed indicate that compounds of Formula I bind selectively to the dopamine D3 receptor. Thus, the compounds of Formula I were tested for their ability to bind to dopamine receptors as measured by their inhibition of [$^3$H]spiperone binding to the human D2 and D3 receptors in a receptor assay described by MacKenzie R. G., et al., Characterization of the human D3 dopamine receptor expressed in transfected cell lines, *Eur. J. Pharmacol.*, 266:79 (1994); and for their ability to inhibit locomotor activity in mice and rats, a measure of antipsychotic activity, according to the assay described by McLean J. R., et al., *Pharmacology, Biochemistry and Behavior*, 8:97–99 (1978). The above test methods are incorporated herein by reference. The data in Table 1 show the dopamine receptor binding activity of representative compounds of Formula I. The data in Table 2 show the locomotor activity of selected compounds of Formula I and demonstrate their utility as antipsychotic agents.

TABLE 1

Receptor Binding of Compounds of Formula I

| Example Number | Compound | Inhibition of [$^3$H] Spiperone Binding to Human D3 Receptors IC$_{50}$, nM | Inhibition of [$^3$H] Spiperone Binding to Human D2 Receptors IC$_{50}$, nM |
|---|---|---|---|
| 1 | E-1,1'-(2-butene-1,4-diyl)bis[2-[4-[3-(1-pyrrolidinyl)propoxy]phenyl]-1H-benzimidazole | 9 | 56 |
| 2 | E-(3-{4-[1-(4-{2-[4-(3-dipropylaminopropoxy)-phenyl]benzoimidazol-1-yl}but-2-enyl)-1H-benzoimidazol-2-yl]phenoxy}propyl)dipropylamine | 5 | 343 |
| 3 | Z-(3-4-[1-(4-{2-[4-(3-diethylaminopropoxy)-henyl]benzoimidazol-1-yl}but-2-enyl)-1H-benzoimidazol-2-yl]phenoxy}propyl)diethylamine | 87 | 1518 |
| 4 | (3-{4-[1-(4-{2-[4-(3-diethylaminopropoxy)-phenyl]benzoimidazol-1-ylmethyl}benzyl)-1H-benzoimidazol-2-yl]phenoxy}propyl)diethylamine | 184 | 3438 |
| 5 | E-(3-{4-[1-(4-{2-[4-(3-dimethylaminopropoxy)-phenyl]benzoimidazol-1-yl}but-2-enyl)-1H-benzoimidazol-2-yl]phenoxy}propyl)dimethylamine | 143 | 4985 |
| 6 | E-1,1'-(2-butene-1,4-diyl)bis[2-[4-[3-(1-piperidinyl)propoxy]phenyl]-1H-benzimidazole | 9 | 517 |
| 7 | E-(3-{3-[1-(4-{2-[3-(3-diethylaminopropoxy)-phenyl]benzoimidazol-1-yl}but-2-enyl)-1H-benzoimidazol-2-yl]phenoxy}propyl)diethylamine | 16 | 2454 |
| 8 | E-dibutyl-(3-{4-[1-(4-{2-[4-(3-dibutylaminopropoxy)phenyl]benzoimidazol-1-yl}but-2-enyl)- | 8 | 427 |

TABLE 1-continued

Receptor Binding of Compounds of Formula I

| Example Number | Compound | Inhibition of [$^3$H] Spiperone Binding to Human D3 Receptors IC$_{50}$, nM | Inhibition of [$^3$H] Spiperone Binding to Human D2 Receptors IC$_{50}$, nM |
|---|---|---|---|
|  | 1H-benzoimidazol-2-yl]phenoxy}propyl)amine |  |  |
| 9 | E-isopropyl-[3-(4-{1-[4-(2-{4-[3-(isopropyl-methylamino)propoxy]phenyl}benzoimidazol-1-yl)but-2-enyl]-1H-benzoimidazol-2-yl}phenoxy)propyl]methylamine | 6 | 200 |
| 10 | E-(3-{4-[1-(4-{2-[4-(3-diethylaminopropoxy)-phenyl]benzoimidazol-1-yl}but-2-enyl)-1H-benzoimidazol-2-yl]phenoxy}propyl)diethylamine | 16 | 2345 |
| 11 | (3-{4-[1-(4-{2-[4-(3-dipropylaminopropoxy)-phenyl]benzoimidazol-1-yl}butyl)-1H-benzoimidazol-2-yl]-phenoxy}propyl)dipropylamine | 16 | 2735 |
| 12 | (3-{4-[1-(4-{2-[4-(3-diethylaminopropoxy)-phenyl]benzoimidazol-1-yl}butyl)-1H-benzoimidazol-2-yl]phenoxy}propyl)diethylamine | 36 | 1070 |
| 13 | diethyl-[3-(4-{1-[4-(2-phenylbenzoimidazol-1-yl)but-2-enyl]-1H-benzoimidazol-2-yl}-phenoxy)propyl]amine | 133 | 6429 |
| 14 | diethyl-{3-[4-(1-{4-[2-(4-methoxyphenyl)-benzoimidazol-1-yl]but-2-enyl}-1H-benzoimidazol-2-yl)phenoxy]propyl}amine | 26 | 1414 |
| 15 | E-[3-(4-{1-[4-(2-{4-[3-(4-phenylpiperazin-1-yl)propoxy]phenyl}benzoimidazol-1-yl)but-2-enyl]-1H-benzoimidazol-2-yl}phenoxy)-propylamine | 19 | 803 |
| 16 | 4,4'-(1,4-butanediyldi-1H-benzimidazol-1,2-diyl)bis[N-[(1-ethyl-2-pyrrolidinyl)-methyl]benzamide | 85 | 1426 |
| 17 | 4,4'-(1,4-butanediyldi-1H-benzimidazol-1,2-diyl)bis[N-[2-(diethylamino)ethyl]benzamide | 110 | 3070 |

TABLE 2

Locomotor Activity of Selected Compounds of Formula I

| Example Number | Compound | Inhibition of Locomotor Activity in Rats ED$_{50}$, mg/kg, IP |
|---|---|---|
| 10 | E-(3-{4-[1-(4-{2-[4-(3-diethylaminopropoxy)phenyl]-benzoimidazol-1-yl}but-2-enyl)-1H-benzoimidazol-2-yl]phenoxy}propyl)diethylamine | 3.9 |
| 12 | (3-{4-[1-(4-{2-[4-(3-diethylaminopropoxy)phenyl]-benzoimidazol-1-yl}butyl)-1H-benzoimidazol-2-yl]-phenoxy}propyl)diethylamine | 2.8 |

A compound of Formula Ia

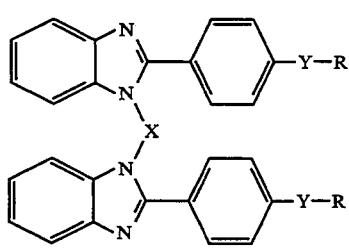

Ia wherein R is

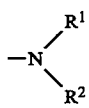

wherein
R$^1$ and R$^2$ are each the same or different and each is alkyl of from 1 to 6 carbon atoms,
alkenyl of from 2 to 6 carbon atoms,
alkynyl of from 2 to 6 carbon atoms,
arylalkyl wherein alkyl is from 1 to 6 carbon atoms,
2-thienylalkyl wherein alkyl is from 1 to 6 carbon atoms or R$^1$ and R$^2$ together with the nitrogen which they substitute
form a 5-membered or 6-membered ring;
X is
alkyl of from 2 to 6 carbon atoms,
alkenyl of from 2 to 6 carbon atoms, or
alkynyl of from 2 to 6 carbon atoms;
Y is —O(CH$_2$)$_n$—wherein n is an integer of from 2 to 6;
and corresponding isomers thereof; or a pharmaceutically acceptable acid addition salt thereof may be prepared by reacting a compound of Formula II

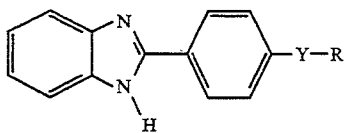
II where R and Y are as defined above in a solvent such as, for example, dimethylformamide and the like with a strong base such as, for example, sodium hydride, butyllithium and the like followed by treatment with a compound of Formula III Hal-X-Hal    III wherein Hal is halogen and X is as defined above at about 0° C. to about 100° C. for about 1 hour to about 24 hours. Preferably, the reaction is carried out in dimethylformamide at room temperature for 18 hours.

A compound of Formula Ib

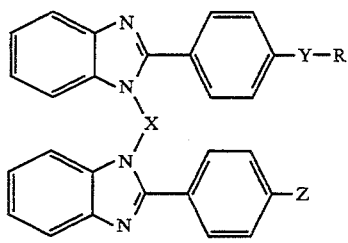
Ib wherein R is

wherein
R$^1$ and R$^2$ are each the same or different and each is
  alkyl of from 1 to 6 carbon atoms,
  alkenyl of from 2 to 6 carbon atoms,
  alkynyl of from 2 to 6 carbon atoms,
  arylalkyl wherein alkyl is from 1 to 6 carbon atoms,
  2-thienylalkyl wherein alkyl is from 1 to 6 carbon atoms or R$^1$ and R$^2$ together with the nitrogen which they substitute form a 5-membered or 6-membered ring;
X is
  alkyl of from 2 to 6 carbon atoms,
  alkenyl of from 2 to 6 carbon atoms, or
  alkynyl of from 2 to 6 carbon atoms;
Y is —O(CH$_2$)$_n$-wherein n is an integer of from 2 to 6;
Z is
  hydrogen,
  hydroxyl,
  alkyl of from 1 to 6 carbon atoms, or
  alkoxy of from 1 to 6 carbon atoms;
and corresponding isomers thereof; or a pharmaceutically acceptable acid addition salt thereof may be prepared by reacting a 1:1 mixture of a compound of Formula II and a compound of Formula IV

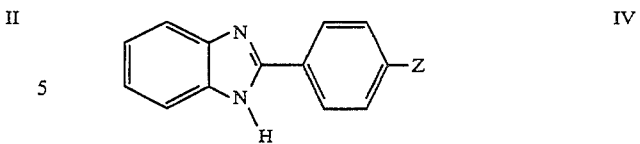
IV wherein Z is as defined above with a strong base such as, for example, sodium hydride, butyllithium and the like in a solvent such as, for example, dimethylformamide and the like followed by treatment with a compound of Formula III at about 0° C. to about 100° C. for about 1 hour to about 24 hours. Preferably, the reaction is carried out in dimethylformamide at room temperature for 18 hours.

A compound of Formula Ic

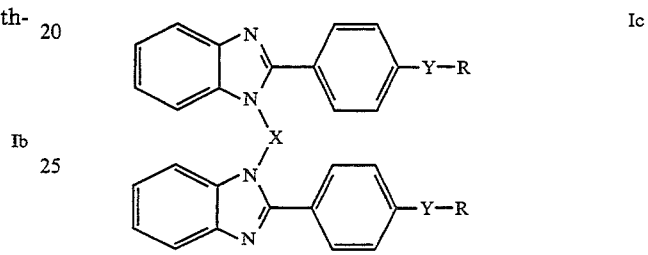
Ic wherein R is

wherein
R$^1$ and R$^2$ are each the same or different and each is
  alkyl of from 1 to 6 carbon atoms,
  alkenyl of from 2 to 6 carbon atoms,
  alkynyl of from 2 to 6 carbon atoms,
  arylalkyl wherein alkyl is from 1 to 6 carbon atoms,
  2-thienylalkyl wherein alkyl is from 1 to 6 carbon atoms or R$^1$ and R$^2$ together with the nitrogen which they substitute form a 5-membered or 6-membered ring, or

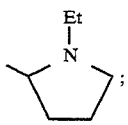

X is
  alkyl of from 2 to 6 carbon atoms,
  alkenyl of from 2 to 6 carbon atoms, or
  alkynyl of from 2 to 6 carbon atoms;
Y is

wherein p is zero or an integer of from 1 to 6;
and corresponding isomers thereof; or a pharmaceutically acceptable acid addition salt thereof may be prepared by reacting a compound of Formula V

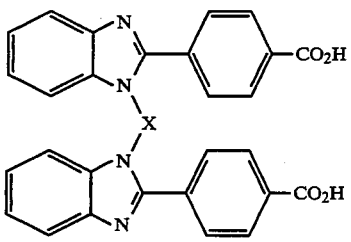

wherein X is as defined above with an amide coupling agent such as, for example, dicyclohexylcarbodiimide, isobutylchloroformate and the like in a solvent such as, for example, dichloromethane, dimethylformamide and the like with a base such as, for example, triethylamine and the like followed by treatment with a compound of Formula VI

wherein R is

wherein $R^1$ and $R^2$ are as defined above and p is as defined above at about $-30°$ C. to about 50° C. for about 30 minutes to about 24 hours. Preferably, the reaction is carried out with isobutylchloroformate in dichloromethane at about $-20°$ C. for about 4 hours with triethylamine as base.

A compound of Formula II or IV may be prepared by reacting 1,2-diaminobenzene with a compound of Formula VII

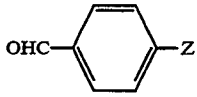

wherein Z is as defined above or Z is Y—R wherein Y and R are as defined above in a solvent such as, for example, nitrobenzene and the like at about 100° C. to about 200° C. for about 1 hour to about 24 hours. Alternatively, the reaction may be carried out in the presence of sodium bisulfite or copper (II) acetate in a solvent such as, for example, methanol and the like at about room temperature to about the reflux temperature of the solvent for about 2 hours to about 24 hours. Preferably, the reaction is carried out with sodium bisulfite in methanol at the reflux temperature for about 6 hours.

A compound of Formula VII is either known or may be prepared by reacting 4-hydroxybenzaldehyde with a strong base such as, for example, sodium hydride, butyllithium and the like in a solvent such as, for example, tetrahydrofuran, dimethylformamide and the like at about 0° C. to about 80° C. followed by treatment with a compound of Formula VIII

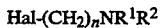

wherein Hal is halogen and n, $R^1$, and $R^2$ are as defined above for about 2 hours to about 24 hours. Preferably, the reaction is carried out in dimethylformamide with sodium hydride at about 60° C. for about 6 hours.

A compound of Formula V may be prepared by treatment of a compound of Formula IX

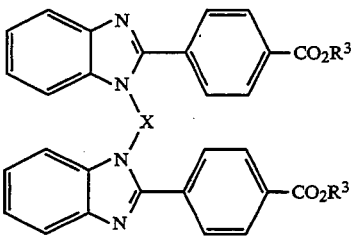

wherein X is as defined above and $R^3$ is alkyl of from 1 to 6 carbon atoms with an alkali metal hydroxide in a solvent such as, for example, tetrahydrofuran and the like in the presence of water at about room temperature to about the reflux temperature of the solvent for about 1 hour to about 24 hours. Preferably, the reaction is carried out with sodium hydroxide in tetrahydrofuran at the reflux temperature for about 2 hours.

A compound of Formula IX may be prepared by the reaction of a compound of Formula X

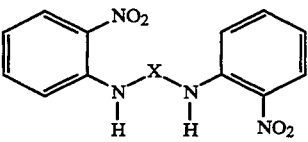

wherein X is as defined above with hydrogen at a pressure of about 1 to 5 atmospheres in the presence of a catalyst such as, for example, palladium on carbon and the like in a solvent such as, for example, an alcohol and the like at about 0° C. to about 50° C. for about 1 hour to about 12 hours. Preferably, the reaction is carried out at about room temperature for 2 hours. The crude product may be treated with a compound of Formula XI

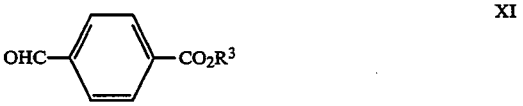

wherein $R^3$ is as defined above in nitrobenzene as solvent at about 100° C. to about 200° C. for about 1 hour to about 24 hours. Alternatively, the reaction may be carried out in the presence of sodium bisulfite or copper (II) acetate in a solvent such as, for example, methanol and the like at from about room temperature to about the reflux temperature of the solvent for about 2 hours to about 24 hours. Preferably, the reaction is carried out with sodium bisulfite in methanol at the reflux temperature for about 6 hours.

A compound of Formula X may be prepared by mixing a compound of Formula XII

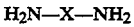

wherein X is as defined above with 1-fluoro-2-nitrobenzene either neat or in the presence of a solvent such as, for example, toluene and the like at about room temperature to about 100° C. for about 1 hour to about 12 hours. Preferably, the reaction is carried out neat at about 70° C. for about 2 hours.

Compounds III, VI, VIII, and XII are either known or capable of being prepared by methods known in the art.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

(E)-1,1'-(2-butene-1,4-diyl)bis[2-[4-[3-(1-pyrrolidinyl)-propoxy]phenyl]-1H-benzimidazole Sodium hydride (0.27 g of 60% in oil) is added to 2-[4-[3-(1-pyrrolidinyl)propoxy]phenyl]-1H-benzimidazole (Example A) (2.00 g) in dimethylformamide (20 mL) and stirred for 30 minutes at 25° C. trans-1,4-Dichloro-2-butene (0.33 mL) is added and the mixture stirred at 25° C. for 14 hours. The mixture is filtered and the solid collected dissolved in chloroform and filtered. The filtrate is evaporated to leave a white solid. The solid is purified by medium pressure liquid chromatography (MPLC) on silica gel eluting with 300:8:1 dichloromethane: ethanol: 0.880 aqueous ammonia to give 0.23 g of the title compound as a white solid; mp 213°–216° C.

In a process analogous to Example 1 using appropriate starting materials, the corresponding compounds of Formula I are prepared as follows:

EXAMPLE 2

E-(3-{4-[1-(4-{2-[4-(3-Dipropylaminopropoxy)phenyl]-benzoimidazol-1-yl}but-2-enyl)-1H-benzoimidazol-2-yl]phenoxy}propyl)dipropylamine; mp 190°–192° C.

EXAMPLE 3

Z-(3-{4-[1-(4-{2-[4-(3-Diethylaminopropoxy)phenyl]-benzoimidazol-1-yl}but-2-enyl)-1H-benzoimidazol-2-yl]phenoxy}propyl)diethylamine; mp 117°–119° C.

EXAMPLE 4

(3-{4-[1-(4-{2-[4-(3-Diethylaminopropoxy)phenyl]-benzoimidazol-1-ylmethyl}benzyl)-1H-benzoimidazol-2-yl]phenoxy}propyl)diethylamine; mp 164°–168° C.

EXAMPLE 5

E-(3-{4-[1-(4-{2-[4-(3-Dimethylaminopropoxy)phenyl]-benzoimidazol-1-yl}but-2-enyl)-1H-benzoimidazol-2-yl]phenoxy}propyl)dimethylamine; mp 203°–206° C.

EXAMPLE 6

E-1,1'-(2-butene-1,4-diyl)bis[2-[4-[3-(1-piperidinyl)-propoxy]phenyl]-1H-benzimidazole; mp 205°–208° C.

EXAMPLE 7

E-(3-{3-[1-(4-{2-[3-(3-Diethylaminopropoxy)phenyl]-benzoimidazol-1-yl}but-2-enyl)-1H-benzoimidazol-2-yl]phenoxy}propyl)diethylamine; mp 152°–154° C.

EXAMPLE 8

E-Dibutyl-(3-{4-[1-(4-{2-[4-(3-dibutylaminopropoxy)-phenyl]benzoimidazol-1-yl}-but-2-enyl)-1H-benzoimidazol-2-yl]phenoxy}propyl)amine; mp 173°–174° C.

EXAMPLE 9

E-Isopropyl-[3-(4-{1-[4-(2-{4-[3-(isopropylmethylamino)propoxy]phenyl}benzoimidazol-1-yl)but-2-enyl]-1H-benzoimidazol-2-yl}phenoxy)propyl]methylamine; mp 189°–190° C.

EXAMPLE 10

E-(3-{4-[1-(4-{2-[4-(3-Diethylaminopropoxy)phenyl]-benzoimidazol-1-yl}but-2-enyl)-1H-benzoimidazol-2-yl]phenoxy}propyl)diethylamine; mp 206°–207° C.

EXAMPLE 11

(3-{4-[1-(4-{2-[4-(3-Dipropylaminopropoxy)phenyl]-benzoimidazol-1-yl}butyl)-1H-benzoimidazol-2-yl]phenoxy}propyl)dipropylamine E-(3-{4-[1-(4-{2-[4-(3-Dipropylaminopropoxy)-phenyl]benzoimidazol-1-yl}but-2-enyl)-1H-benzoimidazol-2-yl]phenoxy}propyl)dipropylamine (Example 2) (100 mg) is hydrogenated at 50 pounds per square inch (psi) in methanol (20 mL) with 20% palladium on carbon (10 mg) for 6 hours. The mixture is filtered and evaporated to leave a yellow solid. The solid is purified by MPLC on silica gel eluting with 200:8:1 dichloromethane:ethanol:0.880 aqueous ammonia to give 49 mg of the title compound as a white solid; mp 141°–143° C.

In a process analogous to Example 11 using appropriate starting materials, the corresponding compound of Formula I is prepared as follows:

EXAMPLE 12

(3-{4-[1-(4-{2-[4-(3-Diethylaminopropoxy)phenyl]ben-zoimidazol-1-yl}butyl)-1H-benzoimidazol-2-yl]phenoxy}propyl)diethylamine; mp 148°–149° C.

EXAMPLE 13

Diethyl-[3-(4-{1-[4-(2-phenylbenzoimidazol-1-yl)but-2-enyl]-1H-benzoimidazol-2-yl}phenoxy)propyl]amine Sodium hydride (0.54 g of 60% in oil) is added to 2-phenylbenzimidazole (1.20 g) and 2-[4-[(3-N,N-diethylamino)propoxy]phenyl]benzimidazole (Example B) (2.00 g) in dimethylformamide (30 mL) and stirred at 20° C. under nitrogen for 1 hour. trans-1,4-Dichloro-2-butene (0.65 mL) is added and the mixture stirred for 18 hours. Water (100 mL) is added and the mixture extracted with dichloromethane (3×50 mL). The extracts are dried over magnesium sulfate, filtered and evaporated to leave a brown oil. The oil is purified by MPLC on silica gel eluting with 200:8:1 dichloromethane:ethanol:0.880 aqueous ammonia to give 0.19 g of the title compound as a white solid; mp 176°–178° C.

In a process analogous to Example 13 using appropriate starting materials, the corresponding compounds of Formula I are prepared as follows:

EXAMPLE 14

Diethyl-{3-[4-(1-{4-[2-(4-methoxyphenyl)ben-zoimidazol-1-yl]-but-2-enyl}-1H-benzoimidazol-2-yl)phenoxy]propyl}amine; mp 190°–192° C.

EXAMPLE 15

E-[3-(4-{1-[4-(2-{4-[3-(4-Phenylpiperazin-1-yl)propoxy]phenyl}benzoimidazol-1-yl)-but-2-enyl]-1H-benzoimidazol-2-yl}phenoxy)propylamine; mp 192°–193° C.

EXAMPLE 16

4,4'-(1,4-butanediyldi-1H-benzimidazol-1,2-diyl)bis[N-[(1-ethyl-2-pyrrolidinyl)methyl]benzamide iso-Butylchloroformate (0.29 mL) is added to 4,4'-(1,4-butanediyldi-1H-benzimidazol-1,2-diyl)benzoic acid (Example C) (0.53 g) and triethylamine (0.34 mL) in dichloromethane (10 mL) at 20° C. under nitrogen with stirring. After 15 minutes, the amine (0.32 mL) is added and the mixture stirred at room temperature for 18 hours. The solvent is evaporated and the residue purified by MPLC on silica gel eluting with 50:8:1 dichloromethane:ethanol:0.880 aqueous ammonia to give 0.13 g of the title compound as a pale yellow solid; mp 106°–108° C.

In a process analogous to Example 16 using appropriate starting materials, the corresponding compound of Formula I is prepared as follows:

EXAMPLE 17

4,4'-(1,4-butanediyldi-1H-benzimidazol-1,2-diyl)bis[N-[2-(diethylamino)ethyl]benzamide; mp 137°–139° C.

PREPARATION OF STARTING MATERIALS

EXAMPLE A

Preparation of 2-[4-[3-(1-pyrrolidinyl)propoxy]phenyl]1H-benzimidazole

Step A: Preparation of 1-(3-Chloropropyl)-1-pyrrolidine

Pyrrolidine (106 mL) is added dropwise to 1-bromo-3-chloropropane (100 g) in diethyl ether (100 mL) while the temperature is kept at 50°-60° C. The mixture is added to 4N hydrochloric acid (700 mL) and washed with diethyl ether (400 mL). The aqueous layer is basified with 2N sodium carbonate and extracted with dichloromethane (2×500 mL). The extracts are dried over magnesium sulfate, filtered and evaporated to leave a yellow oil. The oil is distilled at 110°-120° C./15 mm Hg to give 66.6 g of the title compound as a clear, colorless oil.

Step B: Preparation of 4-[3-(1-pyrrolidinyl)propoxy]-benzaldehyde

Sodium hydride (1.80 g of 60% in oil) is added to 4-hydroxybenzaldehyde (5.00 g) in dimethylformamide (50 mL) and stirred for 20 minutes. 1-(3-Chloropropyl)-1-pyrrolidine (Step A) (7.25 g) is added and the mixture stirred for 14 hours at 60° C. The solvent is evaporated and the residue treated with water (150 mL) and extracted with diethyl ether (2×150 mL). The extracts are dried over magnesium sulfate, filtered and evaporated to leave 10.0 g of the title compound as a yellow solid.

Step C: Preparation of 2-[4-[3-(1-pyrrolidinyl)propoxy]-phenyl]-1H-benzimidazole 1,2-Diaminobenzene (4.65 g), 4-[3-(1-pyrrolidinyl)-propoxy]benzaldehyde (Step B) (10.0 g) and sodium bisulfite (4.60 g) are stirred at reflux in methanol (300 mL) for 14 hours. The mixture is filtered and evaporated. The residue is recrystallized from hot ethyl acetate/ethanol to give 4.68 g of the title compound as a yellow solid.

In a process analogous to Example A using appropriate starting materials, the following compound is prepared.

EXAMPLE B

2-[4-[(3-N,N-Diethylamino)propoxy]phenyl]benzimidazole

EXAMPLE C

Preparation of 4,4'-(1,4-butanediyl-1H-benzimidazol-1,2-diyl)benzoic acid

Step A: Preparation of N,N-(1,4-butanediyl)bis[2-nitrobenzenamine]

1-Fluoro-2-nitrobenzene (43.3 g) is added to a mechanically stirred mixture of 1,4-diaminobutane (15.4 mL) in pyridine (50 mL). The temperature rises to 50° C. and product precipitates out. Dimethylformamide (50 mL) and toluene (50 mL) are added to aid stirring. After addition is complete, the mixture is stirred at 20° C. for 14 hours. The slurry is added to water (500 mL) and filtered. The solid is collected and washed with water (2×100 mL) and dried on the filter. The solid is suspended in hot ethanol (1400 mL) and filtered. The solid is collected and dried at 70° C. under high vacuum to leave 20.1 g of a bright orange solid.

Step B: Preparation of 4,4'-(1,4-butanediyldi-1H-benzimidazol-1,2-diyl)benzoic acid, dimethyl ester N,N'-(1,4-Butanediyl)bis[2-nitrobenzenamine](14.7 g) is hydrogenated at 50 psi in methanol (500 mL) with Raney nickel (5 g). The mixture is filtered and the filtrate added to methyl 4-formylbenzoate (14.7 g) and sodium bisulfite (9.51 g) in methanol (200 mL) at reflux and the mixture stirred at reflux for 6 hours. The cooled mixture is treated with dichloromethane (300 mL) and filtered. The filtrate is evaporated and the residue recrystallized from ethyl acetate/ethanol to give 17.7 g of the title compound as a light brown solid.

Step C: Preparation of 4,4'-(1,4-butanediyldi-1H-benzimidazol-1,2-diyl)benzoic acid 4,4'-(1,4-butanediyldi-1H-benzimidazol-1,2-diyl)benzoic acid, dimethyl ester (5.00 g) and sodium hydroxide (1.79 g) in tetrahydrofuran (50 mL) and water (10 mL) is stirred at reflux for 18 hours. The resulting slurry is added to water (100 mL) and washed with dichloromethane (2×100 mL). The aqueous layer is acidified with hydrochloric acid and the precipitate collected, washed with water, ethyl acetate, and diethyl ether and dried at 70° C./high vacuum to give 4.88 g of the product as a light grey solid.

We claim:

1. A compound of Formula I

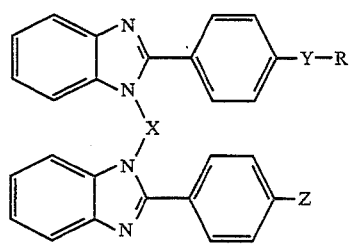

wherein R is

wherein $R^1$ and $R^2$ are each the same or different and each is alkyl of from 1 to 6 carbon atoms,
alkenyl of from 2 to 6 carbon atoms,
alkynyl of from 2 to 6 carbon atoms,
arylalkyl wherein alkyl is from 1 to 6 carbon atoms,
2-thienylalkyl wherein alkyl is from 1 to 6 carbon atoms or $R^1$ and $R^2$ together with the nitrogen which they substitute form a 1-piperidinyl, or 1-pyrrolidinyl ring or R is 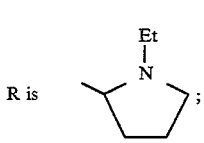

X is
alkyl of from 2 to 6 carbon atoms,
alkenyl of from 2 to 6 carbon atoms, or
alkynyl of from 2 to 6 carbon atoms;

Y is —O(CH$_2$)$_n$— wherein n is an integer of from 2 to 6, or

wherein p is zero or an integer of from 1 to 6; and
Z is hydrogen, hydroxyl, alkyl of from 1 to 6 carbon atoms, alkoxy of from 1 to 6 carbon atoms, or Y—R wherein Y and R are as defined above;

and corresponding isomers thereof; or a pharmaceutically acceptable acid addition salt thereof.

2. A compound according to claim 1, in which

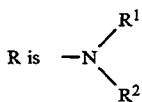

wherein $R^1$ and $R^2$ are each the same or different and each is
methyl,
ethyl,
n-propyl,
isopropyl,
n-butyl,
sec-butyl,
isobutyl,
tert-butyl,
propargyl,
2-phenylethyl,
2-thienyl-2-ethyl or $R^1$ and $R^2$ together with the nitrogen which they substitute form a 1-piperidinyl, or pyrrolidinyl

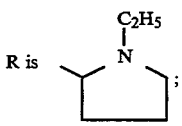

X is n-butyl, or 2-butenyl
Y is —O(CH$_2$)$_2$—,
—O(CH$_2$)$_3$—,
—O(CH$_2$)$_4$—,

Z is
hydrogen,
hydroxyl,
methoxy, or
Y—R wherein Y and R are as defined above.

3. A compound selected from the group consisting of:
E-1,1'-(2-butene-1,4-diyl)bis[2-[4-[3-(1-pyrrolidinyl)-propoxy]phenyl]-1H-benzimidazole;
E-(3-{4-[1-(4-{2-[4-(3-dipropylaminopropoxy)-phenyl]benzoimidazol-1-yl}but-2-enyl)-1H-benzoimidazol-2-yl]phenoxy}propyl)dipropylamine;
Z-(3-{4-[1-(4-{2-[4-(3-diethylaminopropoxy)phenyl]-benzoimidazol-1-yl}but-2-enyl)-1H-benzoimidazol-2-yl]phenoxy}propyl)diethylamine;
(3-{4-[1-(4-{2-[4-(3-diethylaminopropoxy)phenyl]-benzoimidazol-1-ylmethyl}benzyl)-1H-benzoimidazol-2-yl]phenoxy}propyl)diethylamine;
E-(3-{4-[1-(4-{2-[4-(3-dimethylaminopropoxy)-phenyl]benzoimidazol-1-yl}but-2-enyl)-1H-benzoimidazol-2-yl]phenoxy}propyl)dimethylamine;
E-1,1'-(2-butene-1,4-diyl)bis[2-[4-[3-(1-piperidinyl)-propoxy]phenyl]-1H-benzimidazole;
E-(3-{3-[1-(4-{2-[3-(3-diethylaminopropoxy)phenyl]-benzoimidazol-1-yl}but-2-enyl)-1H-benzoimidazol-2-yl]phenoxy}propyl)diethylamine;
E-dibutyl-(3-{4-[1-(4-{2-[4-(3-dibutylaminopropoxy)-phenyl]benzoimidazol-1-yl}but-2-enyl)-1H-benzoimidazol-2-yl]phenoxy}propyl)amine;
E-isopropyl-[3-(4-{1-[4-(2-{4-[3-(isopropylmethylamino)propoxy]phenyl}benzoimidazol-1-yl)but-2-enyl]-1H-benzoimidazol-2-yl}phenoxy)-propyl]methylamine;
E-(3-{4-[1-(4-{2-[4-(3-diethylaminopropoxy)phenyl]-benzoimidazol-1-yl}but-2-enyl)-1H-benzoimidazol-2-yl]phenoxy}propyl)diethylamine;
(3-{4-[1-(4-{2-[4-(3-dipropylaminopropoxy)phenyl]-benzoimidazol-1-yl}butyl)-1H-benzoimidazol-2-yl]phenoxy}proppropyl)dipropylamine;
(3-{4-[1-(4-{2-[4-(3-diethylaminopropoxy)phenyl]-benzimidazol-1-yl}butyl)-1H-benzoimidazol-2-yl]phenoxy}propyl)diethylamine;
diethyl-[3-(4-{1-[4-(2-phenylbenzoimidazol1-yl)but-2-enyl]-1H-benzoimidazol-2-yl}phenoxy)propyl]amine;
diethyl-{3-[4-(1-{4-[2-(4-methoxyphenyl)benzoimidazol-1-yl]but-2-enyl}-1H-benzoimidazol-2-yl)phenoxy]propyl}amine;
E-[3-(4-{1-[4-(2-{4-[3-(4-phenylpiperazin-1-yl)propoxy]phenyl}benzoimidazol-1-yl)but-2-enyl]-1H-benzoimidazol-2-yl}phenoxy)propylamine;
4,4'-(1,4-butanediyldi-1H-benzimidazol-1,2-diyl)-bis[N-[(1-ethyl-2-pyrrolidinyl)methyl]benzamide; and
4,4'-(1,4-butanediyldi-1H-benzimidazol-1,2-diyl)-bis[N-2-(diethylamino)ethyl]benzamide.

4. A method of treating schizophrenia comprising administering to a host suffering therefrom a therapeutic effective amount of a compound according to claim 1 in unit dosage form.

5. A pharmaceutical composition adapted for administration as an agent for treating schizophrenia comprising a therapeutic effective amount of a compound according to claim 1 in admixture with a pharmaceutically acceptable excipient, diluent, or carrier.

* * * * *

UNITED STATES PATENT AND TRADEMARK OFFICE
CERTIFICATE OF CORRECTION

PATENT NO. : 5,414,010
DATED : May 9, 1995
INVENTOR(S) : Downing et al

It is certified that error appears in the above-indentified patent and that said Letters Patent is hereby corrected as shown below:

Column 19, line 26, insert -- 1- -- before "pyrrolidinyl" and insert --ring or-- after "pyrrolidinyl".

Column 19, line 35, insert --;-- after "2-butenyl".

Column 20, line 30, "yl]phenoxy}proppropyl" should read "yl]phenoxy}propyl".

Column 20, line 34, "-phenylbenzoimidazoll-" should read "-phenylbenzoimidazol-1-".

Signed and Sealed this

Fifth Day of December, 1995

Attest:

BRUCE LEHMAN

Attesting Officer        Commissioner of Patents and Trademarks